United States Patent [19]

Miyamae

[11] 4,206,655
[45] Jun. 10, 1980

[54] PRESSURE SENSOR WHICH CAN COMPENSATE FOR TEMPERATURE VARIATION

[75] Inventor: Ryuichi Miyamae, Yamatokoriyama, Japan

[73] Assignee: Sharp Kabushiki Kaisha, Osaka, Japan

[21] Appl. No.: 2,215

[22] Filed: Jan. 9, 1979

[30] Foreign Application Priority Data

Jan. 11, 1978 [JP]  Japan ................................. 53-2100

[51] Int. Cl.² .............................................. G01L 19/04
[52] U.S. Cl. ......................................... 73/708; 73/728
[58] Field of Search ................. 73/708, 704, 703, 702, 73/728; 128/748, 673, 675

[56] References Cited

U.S. PATENT DOCUMENTS

| | | | |
|---|---|---|---|
| 3,242,738 | 3/1966 | Bellier | 73/708 |
| 3,543,585 | 12/1970 | Brown | 73/704 |
| 4,074,576 | 2/1978 | Bryzzhev et al. | 73/702 |

*Primary Examiner*—Donald O. Woodiel
*Attorney, Agent, or Firm*—Birch, Stewart, Kolasch & Birch

[57] ABSTRACT

A pressure sensor comprising pressure responsive means wherein its location is shifted in response to variations of a pressure to be detected, and frequency variation means for varying an oscillation frequency of an oscillator in response to a shift movement of the pressure responsive means. The pressure responsive means and the frequency variation means are mounted on a single supporting table. The single supporting table shows a thermal expansion substantially identical with the total thermal expansion of the pressure responsive means and the frequency variation means, thereby stabilizing a pressure detection.

7 Claims, 1 Drawing Figure

U.S. Patent
Jun. 10, 1980
4,206,655
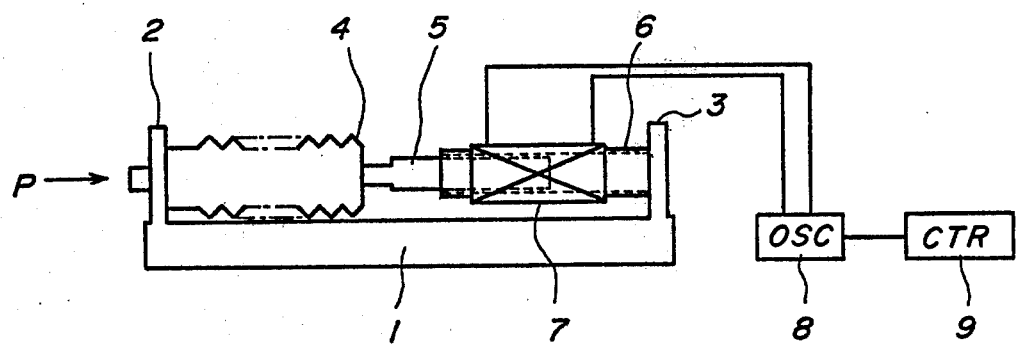

PRESSURE SENSOR WHICH CAN COMPENSATE FOR TEMPERATURE VARIATION

BACKGROUND AND SUMMARY OF THE INVENTION

The present invention relates to a pressure sensor and, more particularly, to a pressure sensor which can compensate for a temperature variation.

A pressure sensor is proposed, which develops a signal of which frequency varies in response to variations of a detected pressure. Such a digital pressure sensor is applicable to a sphygmomanometer including a digital display. A typical digital pressure sensor of the above-mentioned type is described in my copending application Ser. No. 946,089 "DIGITAL PRESSURE SENSOR" filed on Sept. 26, 1978. In such a digital pressure sensor, there is a possibility that the output frequency varies, without regard to the variation of the detected pressure, when a temperature varies. This will preclude an accurate pressure detection.

Accordingly, an object of the present invention is to provide a pressure sensor which can compensate for a temperature variation.

Another object of the present invention is to provide a pressure sensor suited for a sphygmomanometer including a digital display.

Still another object of the present invention is to provide a pressure sensor of a simple construction, and which ensures an accurate pressure detection.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

To achieve the above objects, pursuant to an embodiment of the present invention, a bellows responsive to a pressure to be detected and a frequency variation means for varying an oscillation frequency of an oscillator in response to variations of the detected pressure are disposed on a supporting table. The supporting table is so constructed as to show the thermal expansion which corresponds to the total thermal expansion of the bellows and the frequency variation means. More specifically, the total thermal expansion, due to temperature variations, of the bellows and the frequency variation means in a predetermined direction is identical with that of the supporting table in the same direction.

In a preferred form, the supporting table is made of aluminum and shows the thermal expansion of $2.7 \times 10^{-3}$ mm when the temperature increases by 1° C. The bellows is made of phosphor bronze and shows the thermal expansion of $4 \times 10^{-4}$ mm when the temperature increases by 1° C. The frequency variation means comprises a core attached to the bellows and a winding wound around a bobbin which is secured around the core. The core is made of ferrite and shows the thermal expansion of $2 \times 10^{-4}$ mm when the temperature increases by 1° C., and the bobbin is made of a phenol resin material and shows the thermal expansion of $2.1 \times 10^{-3}$ mm when the temperature increases by 1° C.

BRIEF DESCRIPTION OF THE DRAWING

The present invention will be better understood from the detailed description given hereinbelow and the accompanying drawing which is given by way of illustration only, and thus is not limitative of the present invention and wherein:

The single FIGURE of the drawing is a schematic front view of an embodiment of a pressure sensor of the present invention.

DESCRIPTION OF THE PREFERRED EMBODIMENTS

The single FIGURE of the drawing shows an embodiment of a pressure sensor of the present invention.

A supporting table 1 comprises a flat table and standing ends 2 and 3 for securing pressure detecting elements. A bellows 4 is responsive to a pressure P to be detected. One end of the bellows 4 is secured to the standing end 2. The other end of the bellows 4 is attached to a core 5 which is slidably secured in a bobbin 6. One end of the bobbin 6 is secured to the standing end 3. A coil winding 7 is wound around the bobbin 6.

The coil winding 7 is connected to an oscillator 8 so that an oscillation frequency of the oscillator 8 varies in response to the shift movement of the core 5 within the bobbin 6. An output signal of the oscillator 8 is applied to a counter 9, whereby the contents stored in the counter 9 represent the detected pressure. Detailed constructions of the oscillator 8 and the counter 9 are described in my copending application Ser. No. 946,089 "DIGITAL PRESSURE SENSOR" filed on Sept. 26, 1978.

The supporting table 1 is made of aluminum, the bellows 4 is made of phosphor bronze, the core 5 is made of ferrite, and the bobbin 6 is made of a phenol resin material. The respective elements are so constructed as to have a size which shows the following thermal expansion ($\alpha$, $\beta$, $\gamma$, $\sigma$), when the temperature increases by 1° C., in the direction corresponding to the shift movement of the core 5.

| ($\alpha$) | supporting table 1 | $2.7 \times 10^{-3}$ mm |
| ($\beta$) | bellows 4 | $4 \times 10^{-4}$ mm |
| ($\gamma$) | core 5 | $2 \times 10^{-4}$ mm |
| ($\delta$) | bobbin 6 | $2.1 \times 10^{-3}$ mm |

More specifically, the total thermal expansion of the bellows 4, the core 5 and the bobbin 6 ($\beta+\gamma+\sigma$), or ($4\times10^{-4}$ mm $+2\times10^{-4}$ mm $+2.1\times10^{-3}$ mm) is identical with the thermal expansion ($\alpha$) of the supporting table 1 ($2.7\times10^{-3}$ mm).

When the pressure P applied to the bellows 4 varies, the bellows 4 inflats or is deflated in the direction corresponding to the shift movement of the core 5 in accordance with the pressure variation. Accordingly, the core 5 is shifted within the bobbin 6 in response to the variation of the pressure P. Therefore, the inductance value of the coil winding 7 varies and, hence, the oscillation frequency of the oscillator 8 varies.

In a situation where the temperature varies, the bellows 4, the core 5 and the bobbin 6 show particular thermal expansions. However, these thermal expansions are identical with that of the supporting table 1. Accordingly, the shift movement of the core 5 within the bobbin 6 will not be influenced by the temperature variations. The bellows 4, core 5, bobbin 6 and windings 7 function as a pressure-to-impedance transducer to vary an oscillation frequency of the oscillator 8 in response to variations in the pressure P.

The above-mentioned embodiment utilizes the inductance variation for detecting pressure. However, the variation of the capacitance or the resistance can be used for detecting the pressure.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A pressure sensor comprising:
   an oscillator;
   a pressure-to-impedance transducer for varying an oscillation frequency of said oscillator in response to variations of a pressure to be detected;
   supporting means for supporting said pressure-to-impedance transducer, said supporting means functioning to absorb a thermal expansion of said pressure-to-impedance transducer mounted thereon; and
   said supporting means comprises a supporting table having a specific coefficient of expansion and shape to achieve a thermal expansion substantially identical with the thermal expansion of said pressure-to-impedance transducer.

2. A pressure sensor comprising:
   an oscillator;
   shift means wherein its location is shifted in response to variations of a pressure to be detected;
   frequency variation means for varying an oscillation frequency of said oscillator in response to a shift movement of said shift means; and
   supporting means for supporting both said shift means and said frequency variation means on a single integral supporting table;
   said single integral supporting table having a specific coefficient of expansion and a shape to achieve a thermal expansion substantially identical with a total thermal expansion of said shift means and said frequency variation means.

3. The pressure sensor of claim 2, wherein said supporting means including:
   a first supporting member secured to one end of said single integral supporting table, said shift means being secured to said first supporting member; and
   a second supporting member secured to the opposing end of said single integral supporting table, said frequency variation means being secured to said second supporting member.

4. The pressure sensor of claim 3, wherein said shift means comprising:
   a bellows secured to said first supporting member, said bellows responding to the pressure to be detected; and
   a core attached to said bellows so that said core shifts its position along its axis in response to variations of the pressure to be detected, and
   said frequency variation means comprising:
   a bobbin secured to said second supporting member, said core being movable within said bobbin along their axes; and
   a coil winding wound around said bobbin, said coil winding being connected to said oscillator for varying said oscillation frequency in response to a shift movement of said core within said bobbin.

5. The pressure sensor of claim 4, wherein said total thermal expansion of said bellows ($\beta$), the core ($\gamma$) and the bobbin ($\sigma$) is substantially identical with the thermal expansion of said single integral supporting table ($\alpha$), that is, $$\alpha/°C. \approx \beta/°C. + \gamma/°C. + \sigma/°C.$$

6. The pressure sensor of claim 5, wherein said thermal expansions $\alpha$, $\beta$, $\gamma$ and $\sigma$ are as follows:
   $\alpha = 2.7 \times 10^{-3}$ mm (/°C.)
   $\beta = 4 \times 10^{-4}$ mm (/°C.)
   $\gamma = 2 \times 10^{-4}$ mm (/°C.)
   $\sigma = 2.1 \times 10^{-3}$ mm (/°C.).

7. The pressure sensor of claim 4, 5 or 6, wherein said bellows comprises a phosphor bronze bellows; said core comprises a ferrite core; said bobbin comprises a phenol resin bobbin; and said single integral supporting table comprises an aluminum flat table.

* * * * *